United States Patent
Nakao

(10) Patent No.: US 7,346,600 B2
(45) Date of Patent: Mar. 18, 2008

(54) DATA ANALYZER

(75) Inventor: Yoshio Nakao, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 463 days.

(21) Appl. No.: 11/038,541

(22) Filed: Jan. 21, 2005

(65) Prior Publication Data

US 2005/0125201 A1    Jun. 9, 2005

Related U.S. Application Data

(63) Continuation of application No. PCT/JP03/01576, filed on Feb. 14, 2003.

(51) Int. Cl.
*G06F 7/00* (2006.01)

(52) U.S. Cl. ......................................................... 707/1

(58) Field of Classification Search ...................... 707/1
See application file for complete search history.

(56) References Cited

U.S. PATENT DOCUMENTS

2003/0068825 A1 * 4/2003 Washburn et al. ............ 436/86

FOREIGN PATENT DOCUMENTS

EP    1 089 211    4/2001

JP    2000-99746    4/2000
JP    2001-281244    10/2001

OTHER PUBLICATIONS

Kasif, S., "Datascope: Mining Biological Sequences", IEEE Intelligent Systems & their Applications, vol. 14, No. 6.
A. Konagaya, "Current Status and Issues of Bioinformatics", Proceedings of the 45th Annual Conference of the Institute of Systems, Control and Information Engineers (ISCIE); 2001; pp. 27-30.
Notice of Rejection Grounds for Japanese Application No. 2004-568192; mailed Mar. 14, 2006.

* cited by examiner

*Primary Examiner*—Chong H Kim
(74) *Attorney, Agent, or Firm*—Staas & Halsey LLP

(57) ABSTRACT

A data analysis unit outputs a plurality of the analytical results by performing various analyses on analytical data concerning a set of analytical objects from different viewpoints and different grading for re-arrangement and systematization of analytical objects. In a knowledge storage unit, the information expressing the background knowledge which can be utilized by the user is stored for each analytical object beforehand. An analytical result selection unit analyzes relationships between the analytical results output from the data analysis unit and the information stored in the knowledge storage unit, selects those results which have a high consistency with the background knowledge, and presents the selected analytical results to the user.

10 Claims, 17 Drawing Sheets

| FACTOR / GENE | CONDITION 1 | CONDITION 2 | ... | CONDITION n |
|---|---|---|---|---|
| gene-1 | d(1, 1) | d(1, 2) | ... | d(1, n) |
| gene-2 | d(2, 1) | d(2, 2) | ... | d(2, n) |
| ⋮ | ⋮ | ⋮ | ⋮ | ⋮ |
F I G. 6 A
| FACTOR / GENE | e-1 | e-2 | ... | e-n |
|---|---|---|---|---|
| gene-1 | v(1, 1) | v(1, 2) | ... | v(1, n) |
| gene-2 | v(2, 1) | v(2, 2) | ... | v(2, n) |
| ⋮ | ⋮ | ⋮ | ⋮ | ⋮ |
F I G. 6 B
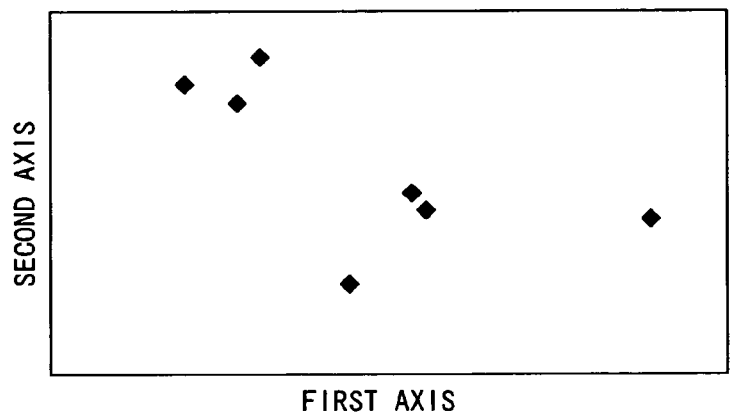
F I G. 6 C

| FIELD NAME | TYPE | VALUE |
|---|---|---|
| ID | ID | GRAA_HUMAN |
| DESCRIPTION | Text | Granzyme A precursor (EC 3.4.21.78) |
| RELEVANT GENE | Text | GZMA OR CTLA3 OR HFSP |
| MOLECULAR WEIGHT | NUMERIC VALUE | 28968 |
| AMINO ACID | SEQUENCE DATA | MRNSYRFLAS SLSVVVSLLL... |

F I G. 7

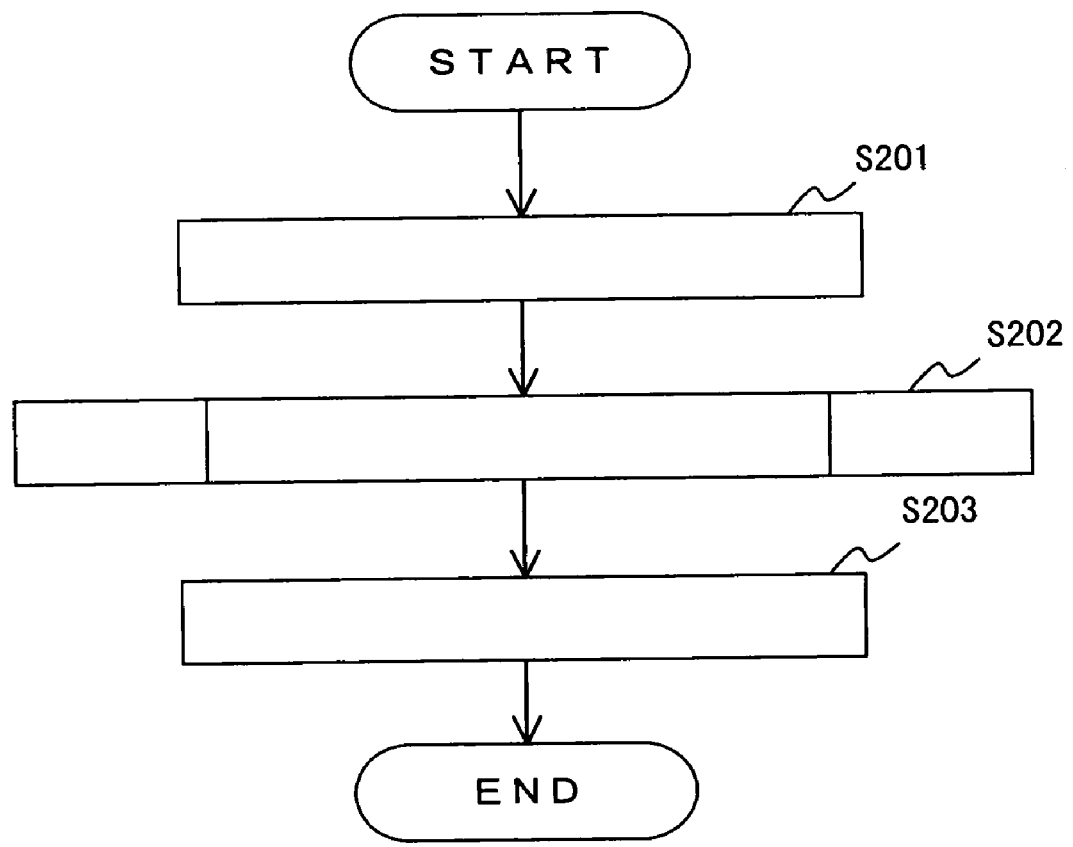
F I G. 8

| GENE \ ATTRIBUTE | e-1 | e-2 | ... | e-n |
|---|---|---|---|---|
| gene-1 | v(1,1) | v(1,2) | ... | v(1,n) |
| gene-2 | v(2,1) | v(2,2) | ... | v(2,n) |
| ⋮ | ⋮ | ⋮ | ⋮ | ⋮ |

F I G. 1 2 A

| GENE \ ATTRIBUTE | ATTRIBUTE 1 | ATTRIBUTE 2 | ... | ATTRIBUTE m |
|---|---|---|---|---|
| gene-1 | f(1,1) | f(1,2) | ... | f(1,m) |
| gene-2 | f(2,1) | f(2,2) | ... | f(2,m) |
| ⋮ | ⋮ | ⋮ | ⋮ | ⋮ |

F I G. 1 2 B

| FACTOR \ ATTRIBUTE | ATTRIBUTE 1 | ATTRIBUTE 2 | ... | ATTRIBUTE m |
|---|---|---|---|---|
| e-1 | $\Sigma v(i,1)*f(i,1)$ | $\Sigma v(i,1)*f(i,2)$ | ... | $\Sigma v(i,1)*f(i,m)$ |
| e-2 | $\Sigma v(i,2)*f(i,1)$ | $\Sigma v(i,2)*f(i,2)$ | ... | $\Sigma v(i,2)*f(i,m)$ |
| ⋮ | ⋮ | ⋮ | ⋮ | ⋮ |
| e-n | $\Sigma v(i,n)*f(i,1)$ | $\Sigma v(i,n)*f(i,2)$ | ... | $\Sigma v(i,n)*f(i,m)$ |

F I G. 1 2 C

| FACTOR / GENE | e-1 | e-2 |
|---|---|---|
| gene-1 | .6 | .1 |
| gene-2 | .4 | .3 |

F I G. 1 3 A

| ATTRIBUTE / GENE | ATTRIBUTE 1 | ATTRIBUTE 2 | ... | ATTRIBUTE m |
|---|---|---|---|---|
| gene-1 | 5 | 20 | ... | 0 |
| gene-2 | 15 | 0 | ... | .8 |

F I G. 1 3 B

| ATTRIBUTE / FACTOR | ATTRIBUTE 1 | ATTRIBUTE 2 | ... | ATTRIBUTE m |
|---|---|---|---|---|
| e-1 | .6*5+.4*15 | .6*20+.4*0 | ... | .6*0+.4*.8 |
| e-2 | .1*5+.3*15 | .1*20+.3*0 | ... | .1*0+.3*.8 |

F I G. 1 3 C

| ATTRIBUTE / FACTOR | ATTRIBUTE 1 | ATTRIBUTE 2 | ... | ATTRIBUTE m |
|---|---|---|---|---|
| e-1 | $\Sigma v(i,1)*f(i,1)$ | $\Sigma v(i,1)*f(i,2)$ | ... | $\Sigma v(i,1)*f(i,m)$ |
| e-2 | $\Sigma v(i,2)*f(i,1)$ | $\Sigma v(i,2)*f(i,2)$ | ... | $\Sigma v(i,2)*f(i,m)$ |
| ⋮ | ⋮ | ⋮ | ⋮ | ⋮ |
| e-n | $\Sigma v(i,n)*f(i,1)$ | $\Sigma v(i,n)*f(i,2)$ | ... | $\Sigma v(i,n)*f(i,m)$ |

FIG. 14A

| SYNTHESIZED FACTOR / FUNDAMENTAL FACTOR | c-1 (First axis) | c-2 (Second axis) | ... | c-m (m-th axis) |
|---|---|---|---|---|
| e-1 | w(1,1) | w(1,2) | ... | w(1,m) |
| e-2 | w(2,1) | w(2,2) | ... | w(2,m) |
| ⋮ | ⋮ | ⋮ | ⋮ | ⋮ |
| e-n | w(n,1) | w(n,2) | ... | w(n,m) |

FIG. 14B

| SYNTHESIZED FACTOR<br>FUNDA-<br>MENTAL FACTOR | c-1 | c-2 | ... | c-k | SCORE |
|---|---|---|---|---|---|
| e-1 | w(1,1) | w(1,2) | ... | w(1,k) | $\Sigma w(1,i)$ |
| e-2 | w(2,1) | w(2,2) | ... | w(2,k) | $\Sigma w(2,i)$ |
| ⋮ | ⋮ | ⋮ | ⋮ | ⋮ | ⋮ |
| e-n | w(n,1) | w(n,2) | ... | w(n,k) | $\Sigma w(n,i)$ |

| FUNDA-MENTAL FACTOR \ SYNTHESIZED FACTOR | c-1 | c-2 |
|---|---|---|
| e-1 | w(1, 1) | w(1, 2) |
| e-2 | w(2, 1) | w(2, 2) |
| ⋮ | ⋮ | ⋮ |
| e-n | w(n, 1) | w(n, 2) |

DATA ANALYZER

CROSS REFERENCE TO RELATED APPLICATIONS

This is a continuation of an International application No. PCT/JP2003/001576 filed on Feb. 14, 2003.

BACKGROUND OF THE INVENTION

1. Field of the Invention

The present invention relates to a technology which supports the analysis of data obtained by an experiment or a research.

2. Description of the Related Art

As technology for supporting the analysis of data obtained by an experiment or a research, a technology wherein data is statistically analyzed, similar data is re-arranged and systematized based on the analytical results, and then presented is known. A technology wherein a factor analysis, a form of multivariate analysis, is performed and the relation between data is represented as a scatter diagram and a technology wherein data is clustered according to the similarities between data and represented as a tree diagram are known as typical technologies. These technologies enable users to easily analyze and interpret experimental data since the characteristics of the experimental data can be recognized as patterns.

For example, in regards to gene expression data, a technology is known wherein gene expression pattern and the clustering results of the gene are represented in a form such as that shown in FIG. 1. In FIG. 1, gene expression data 1 is a representative example of a gene expression pattern where the expression level of a gene (vertical axis 1$y$) in an experiment condition (horizontal axis 1$x$) is expressed by the color of the corresponding cell (alternative representation is indicated in FIG. 1 by the darkness of the shading). The tree diagram 2 is a representative example of the results of hierarchical clustering of genes based on the similarities in the expression patterns.

For example, Japanese Patent Laid-Open Publication No. 2001-281244 discloses technology for extracting typical classifications, where broad classifications and classification grading vary significantly, by analyzing the results of the clustering while taking into consideration the "identification error scope" of users. The technology for presenting the information expressing these typical classifications in the tree diagram is also disclosed.

In addition, the Japanese Patent Laid-Open Publication No. 2000-99746 shows technology, in regards to analysis of data with multiple attributes, for detecting attributes suitable for the categorization and visualization of the data characteristics based on the correlation coefficient between the attributes according to the distribution of the attribute values or the like, and presenting information suitable for user analysis.

However, since these technologies make the analytical results to be provided to the user by analyzing the intrinsic nature (or correlation) of the target data, the presented results are not necessarily understandable for the user. That is a problem.

In other words, since typical data analysis technologies, including factor analysis and cluster analysis, can only present possible classification of the data items according to the mutual similarities across the data, the interpretation of the analytical results is left to the user.

For example, in regards to factor analysis, the result can be easily interpreted if it presents such a good factor as most of high score genes for that factor belong to a gene family which produces a kind of enzyme relating to a certain function. However, it is more likely that obtained results are hard for the user to interpret.

Furthermore, even in a cluster analysis, although the data items can be hierarchically classified (see FIG. 1, for example), what meanings the aggregation of data belonging to each hierarchy corresponds to is subjected to the judgment of the user.

Some methods for solving this problem, such as factor rotation (varimax method) in factor analysis, which rotates factors in a direction that is easy to interpret, are known. However, the basic purpose of those methods is to transform the analytical results into as simple a structure as possible, and the knowledge of the user is not considered.

Although the technology disclosed in the afore-mentioned Japanese Patent Laid-Open Publication No. 2001-281244 enables the user to find an appropriate classification result easily by taking into consideration the "identification error scope" specified by the user and combining similar classification results which fall within the identification error scope, the knowledge of the user is not considered.

Furthermore, although the technology disclosed in the afore-mentioned Japanese Patent Laid-Open Publication No. 2000-99746 provides a mechanism for reflecting specifications by the user, such as specifications of the targeted attribute of the analysis, in the classification result, its configuration cannot flexibly reflect the background knowledge of the user because it is difficult or may be impossible for the user to list up all possible specifications relating to the background knowledge beforehand.

The purpose of the present invention is to enable users to efficiently analyze experimental and research data, taking into account the foregoing circumstances.

SUMMARY OF THE INVENTION

The data analyzer, which is one of the embodiments according to the present invention, is a device which supports the analysis of data obtained as the results of an experiment or an investigation performed on a set of objects to be analyzed, and achieves the afore-mentioned purpose by its configuration, which comprises a knowledge storage unit for storing knowledge information which expresses background knowledge for the data analysis, a data analysis unit for obtaining a plurality of analytical results of the data where the analytical objects are re-arranged and systematized based on the mutual similarities shown in the data from different viewpoints, and an analytical result selection unit for evaluating the analytical results of the data based on the knowledge information and for selecting those results which have a higher consistency with the knowledge information.

At this time, for example, the data analysis unit extracts a plurality of explanatory factors by performing a multivariable analysis on the analytical data. The analytical result selection unit first extracts attribute information pertaining to the object of analysis from the knowledge information. Then, this unit calculates a score indicating the degree of consistency between the explanatory factors and the knowledge information by performing multivariable analysis on the explanatory factors and the attribute information, and selection can be performed based on this score.

According to this configuration, the analytical data is analyzed by the data analysis unit from a plurality of viewpoints, and the analytical results which have a higher consistency with the knowledge information stored in the knowledge storage unit are selected by the analysis result selection unit and provided to the user. This enables that the analytical results easy to interpret are preferentially provided to the user, and therefore, the user can efficiently proceed with the analysis of the experiment and research data.

In this configuration, if the knowledge information is a text data that describes the attributes of the object of analysis, the analysis result selection unit is capable of extracting keywords from the text associated with the object of analysis as the attribute information, and then, performing the selection explained above.

According to this configuration, even if the knowledge information is given in text data, the analytical result which can be more easily interpreted by the user can be preferentially provided to the user.

Furthermore, in this configuration, the analysis result selection unit can perform selection by using the attribute information that can be obtained for the predetermined number of objects of analysis or more from the knowledge information.

According to this configuration, since the afore-mentioned selection is performed utilizing the attribute information that can describe the characteristics of many genes, the analytical results which can be more easily interpreted by the user can be provided more adequately to the user.

In addition, in this configuration, the analysis result selection unit can select explanatory factors with a high consistency score and determine the analytical result expressed by the selected explanatory factors to be the result of the selection.

This configuration specifies one of the approaches for presenting the selected analytical results, selects fundamental factors based on synthesized factor scores (described later in the embodiments according to the present invention), and shows a graphical representation of the analytical results by using the selected fundamental factors as the axes of a graph.

In addition, in this configuration, the analysis result selection unit can determine the synthesized explanatory factors which have a higher consistency with the knowledge information based on the afore-mentioned score and determine the analytical results expressed by the synthesized factors to be the selected results.

This configuration specifies another approach for presenting the selected analytical results, and shows a graphical representation of the analytical results by using the more highly descriptive (high contribution rate in regards to the information of the object of analysis) synthesized factors as the axes of the graph (described later in the embodiments according to the present invention).

In addition, in this configuration, the analysis result selection unit can be configured to output the analytical results which are the results of the selection and the afore-mentioned explanatory factor together with the score showing the degree of consistency between the explanatory factor and the knowledge information, and the attribute information.

According to this configuration, it becomes easy for the user to grasp the analytical results.

Furthermore, at this point, the configuration can be made so as to further output the analytical results expressed by the factors which has been specified for selection, out of the afore-mentioned explanatory factors.

By doing so, the analytical results expressed by the explanatory factor specified by the user can be provided to the user.

BRIEF DESCRIPTION OF THE DRAWINGS

The present invention may become clearer if the detailed description described later is referenced together with the following attached drawings.

FIG. 6A is a table showing an example of data to be analyzed;

FIG. 6B is a table showing the results of a factor analysis performed on the data to be analysis shown in FIG. 6A;

FIG. 6C shows a representation example by scatter diagram;

FIG. 7 is a diagram showing examples of knowledge data stored in the protein DB;

FIG. 8 is a flowchart showing the processing details of an acquirement processing for the knowledge data;

FIG. 12A is a table showing the results of the factor analysis;

FIG. 12B is a table showing knowledge data;

FIG. 12C is a table corresponding to the synthesized matrix created by an analytical result selection unit;

FIG. 13A is a table made by giving specific numeric values as a calculation example to the table shown in FIG. 12A;

FIG. 13B is a table made by giving specific numeric values as a calculation example to the table shown in FIG. 12B;

FIG. 13C is a table corresponding to the synthesized matrix by multiplying the matrix corresponding to the table shown in FIG. 13A by the matrix corresponding to the table shown in FIG. 13B;

FIG. 14A is a table for the synthesized matrix expressing the relation between the factors and the attributes;

FIG. 14B is a table showing the results of a factor analysis that was performed in regards to the table in FIG. 14A with the attributes as the variables;

DESCRIPTION OF THE PREFERRED EMBODIMENTS

Described below is the embodiment according to the present invention based on the drawings.

Figure 1:
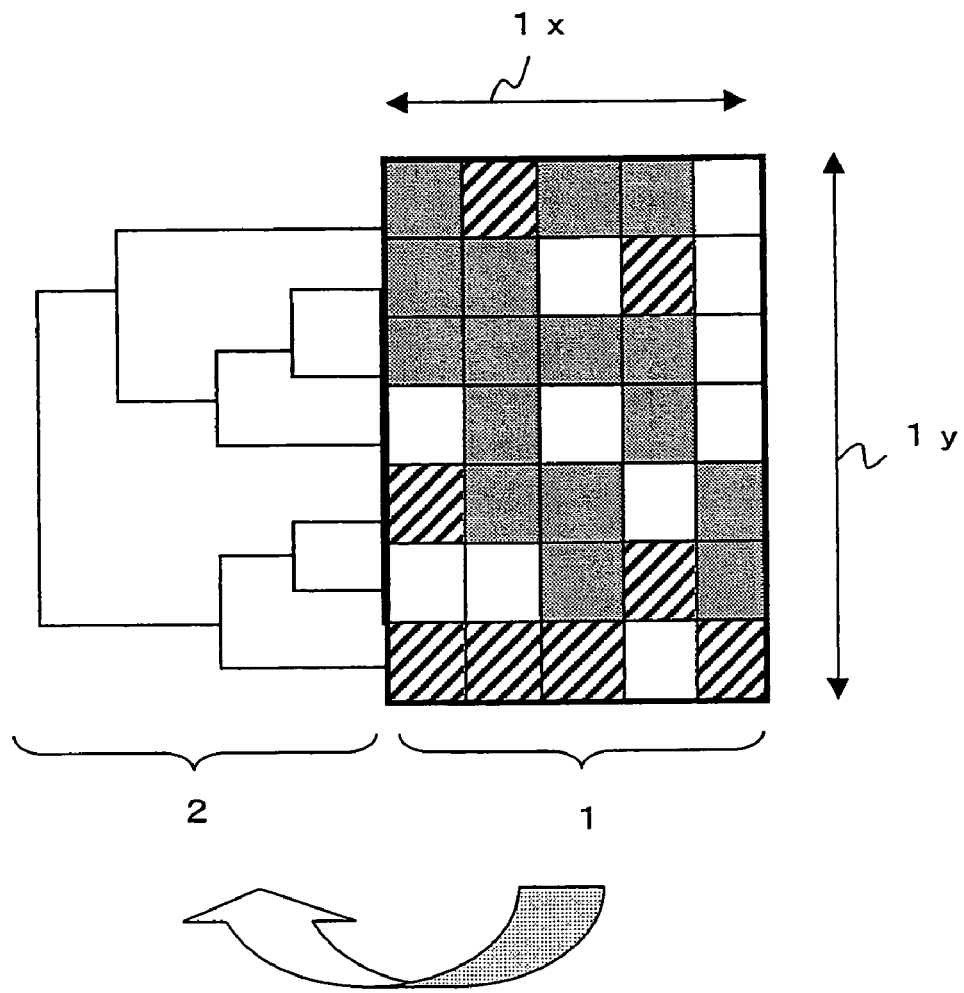
FIG. 1 is a diagram used to describe a related art.
Figure 2:
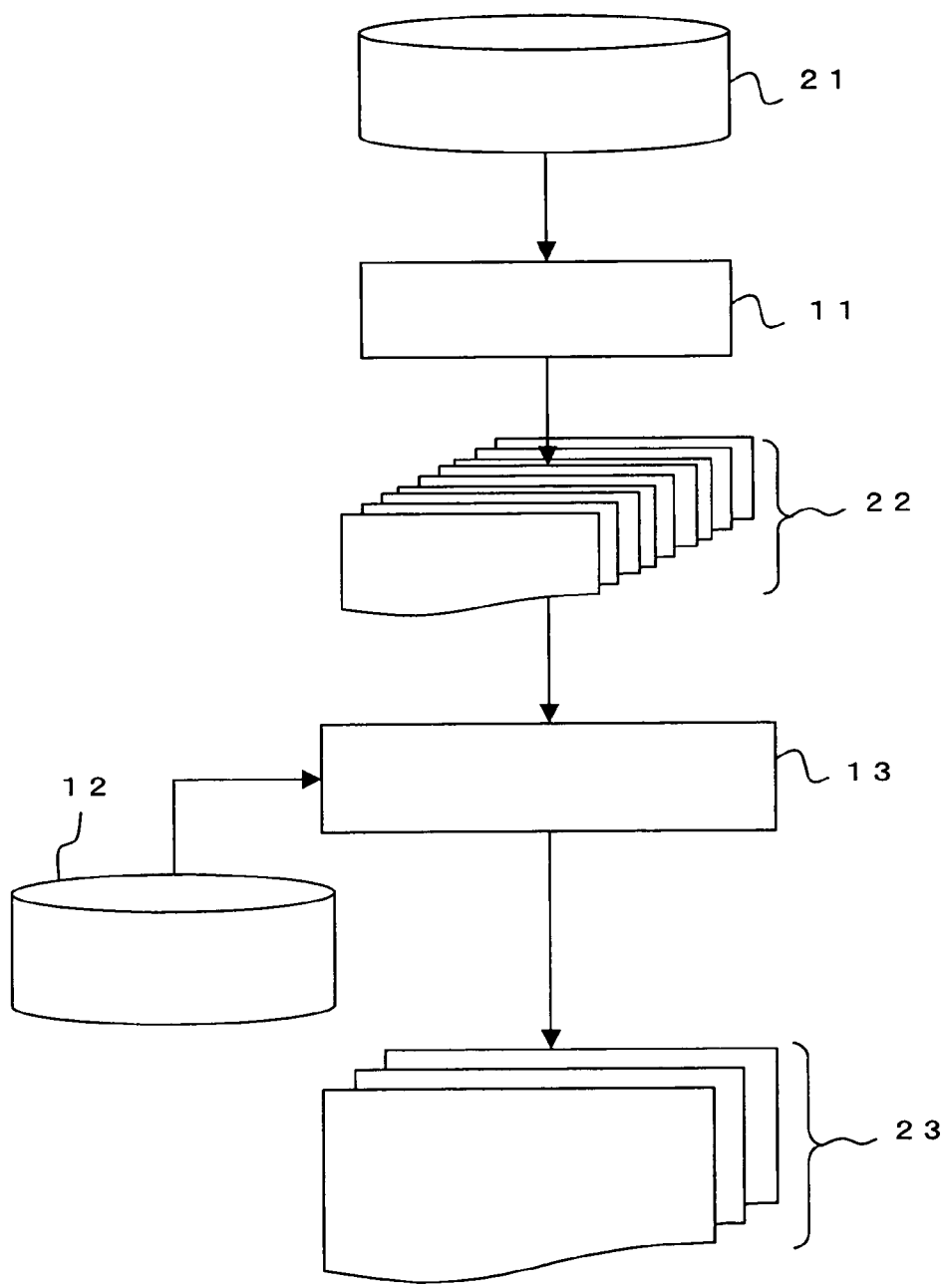
FIG. 2 is a diagram showing the principle configuration of a data analyzer implementing the present invention.

FIG. 2 shows the principle configuration of a data analyzer that implements the present invention. The data analyzer according to the present invention comprises a data analysis unit 11, a knowledge storage unit 12, and an analysis result selection unit 13.

The data analysis unit 11 analyzes a data to be analyzed 21 and outputs analytical results 22 wherein similar data have been re-arranged and systematized. The data analysis unit 11 performs various analyses from different viewpoints and different grading for re-arranging and systemizing data on the same data to be analyzed 21. Therefore, a plurality of analytical results 22 is normally outputted from the data analysis unit 11.

The background knowledge that can be used by the user, for example, the qualities or the like that are known beforehand of the substance (gene or the like) which is the object of data collection is stored in the knowledge storage unit 12 beforehand.

The analysis result selection unit 13 selects the analytical results which have a higher consistency with the background knowledge that can be used by the user, out of the plurality of analytical results 22 output from the data analysis unit 11, guided by the information stored in the knowledge storage unit 12, and presents the selected analytical results to the user as the selected analytical results 23.

In the configuration shown in FIG. 2, first, the data to be analyzed 21 is analyzed by the data analysis unit 21 from a plurality of viewpoints, and the analytical results 22 which are equivalent to the analytical results are prepared. Then, the analytical results which have a higher consistency with the knowledge data stored in the knowledge storage unit 13, out of the analytical results 22, is selected by the analysis result selection unit 13 and are provided to the user as the selected analytical results 23. Since this allows the analytical results which can be more easily interpreted by the user, out of the analytical results 22, to be preferentially provided to the user, the user can efficiently proceed with the analysis of the experiment and research data.

Figure 3:
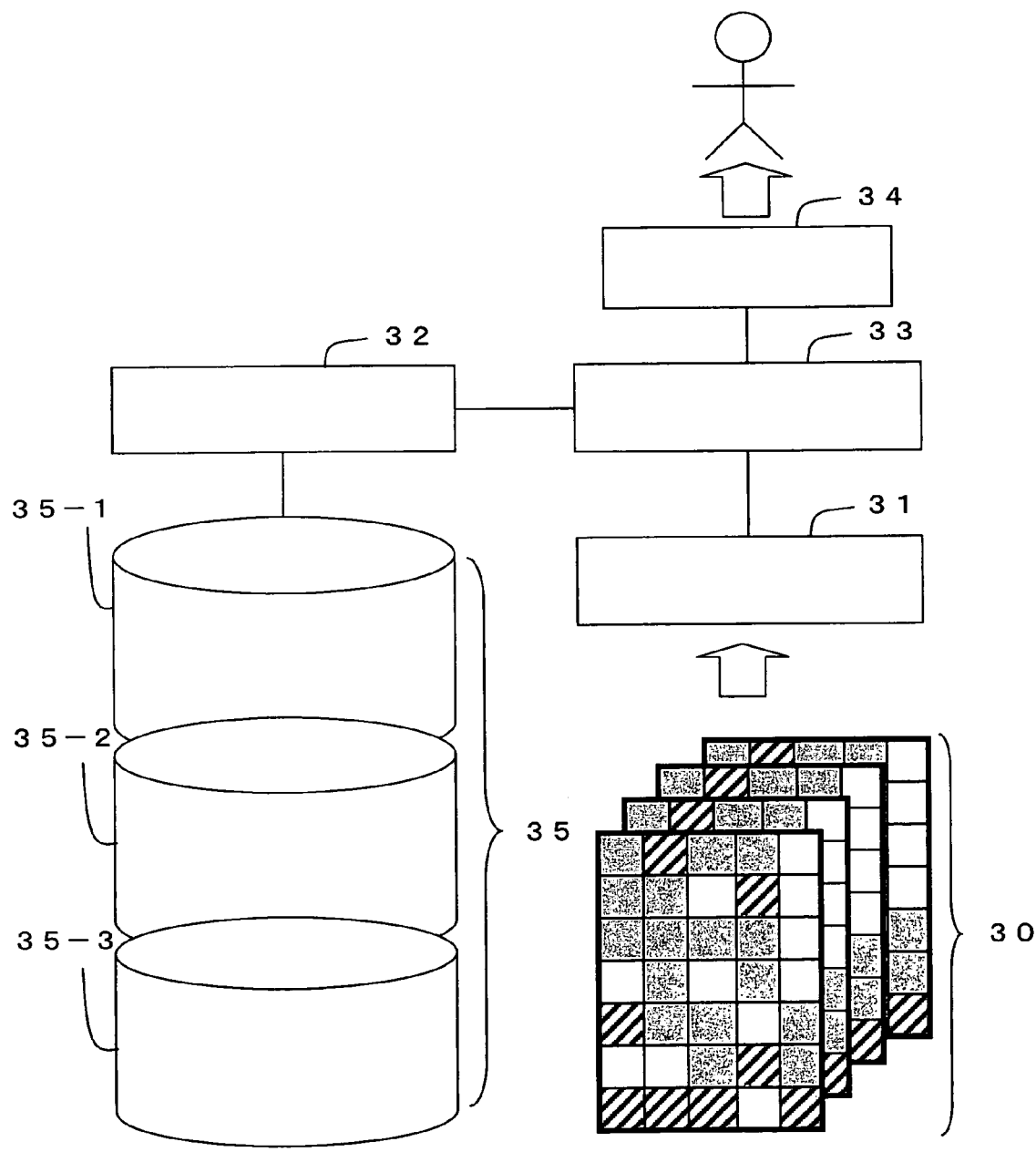
FIG. 3 is a diagram showing the function configuration of a data analyzer implementing the present invention.

Next, described is the function configuration of the data analyzer that implements the present invention shown in FIG. 3.

A data analysis unit 31, equivalent to the data analysis unit 11 in FIG. 2, analyzes experimental data 30, and outputs analytical results wherein similar data have been re-arranged and systematized to an analysis result selection unit 33.

A data management unit 32 manages the knowledge source DB (database) 35 where the background knowledge that can be used by the user is stored beforehand. The user knowledge storage unit 12 is equivalent to the knowledge data management unit 32 and the knowledge source DB 35.

The analysis result selection unit 33, equivalent to the analysis result selection unit 13 in FIG. 2, selects the analytical results which have a higher consistency with the background knowledge that can be used by the user, guided by the information stored in the knowledge source DB 35, out of the analytical results output from the data analysis unit 31, and outputs the selected results to analysis result presentation unit 34.

The analysis result presentation unit 34 indicates the selected analytical results sent from the analysis result selection unit 33 and presents these results to the user.

The knowledge source DB 35 comprises protein DB 35-1 where the attribute information of an amino acid sequence or the like is stored, the gene DB 35-2 where the attribute information of a DNA sequence is stored, and the documents DB 35-3 where information such as theses is stored.

In FIG. 3, the data analysis unit 31 prepares a plurality of the analytical results and sends these results to the analysis result selection unit 33 when the experimental data 30 is input. The analysis result selection unit 33 first obtains, through the knowledge data management unit 32, information (knowledge data) related to the analytical results sent from the data analysis unit 31 and evaluates each analytical result sent from the data analysis unit 31 based on the obtained knowledge data, selects the analytical results which have a higher consistency with the knowledge data out of the evaluated results and sends these results to the analysis result presentation unit 34.

Here, although the analytical results to be sent to the analysis result presentation unit 34 may be only one kind, it is preferable that a plurality of the analytical results, each of which has a degree of consistency with the knowledge data, is sent and is presented to the user, in order to more effectively exert the function of the data analyzer according to the present invention.

The analysis result presentation unit 34 presents the analytical results sent from the analysis result selection unit 33 to the user in visual form such as graphical representation. In addition, if a plurality of the analytical results which have a degree of consistency with the knowledge data is presented, the analytical results which have high consistency are first provided to the user, and subsequently, the next candidate for the analytical result is provided in accordance with the instructions of the user, or the instruction from the user maybe fed back to the analysis result selection unit 33 where a re-selection process is performed on the analytical results. Here, the re-selection processing can be realized, for example, by receiving a keyword specification from the user and re-calculating the degree of consistency between the knowledge data and the analytical results after adding emphasis on the knowledge data related to the keyword.

Figure 4:
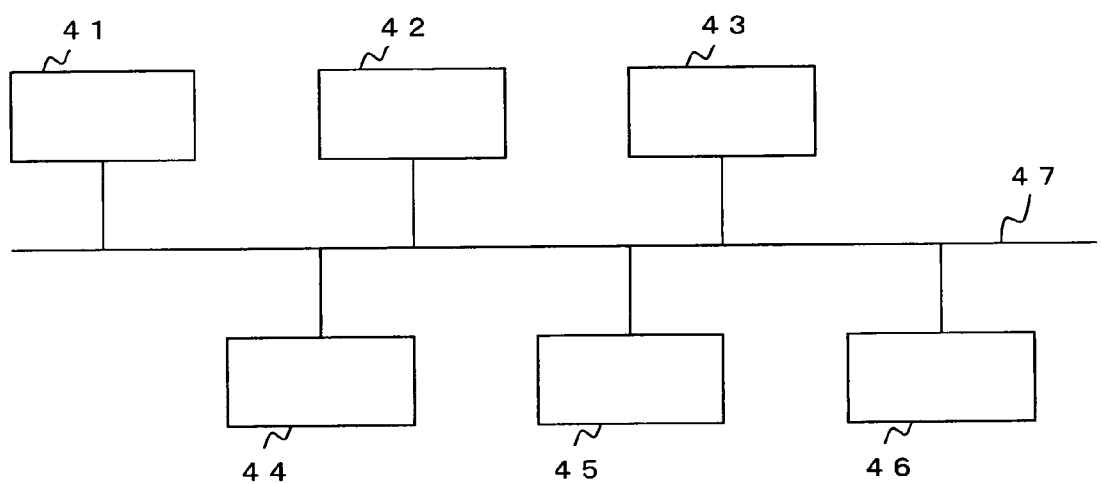
FIG. 4 is a diagram showing the hardware configuration of the data analyzer shown in FIG. 3.

Next, FIG. 4 is described. FIG. 4 is a configuration diagram of the hardware in the data analyzer shown in FIG. 3.

In FIG. 4, CPU 41, ROM 42, RAM 43, HDD 44, an input unit 45, and a display unit 46 are interconnected via bus 47, and data can be mutually transferred under the management of CPU 41.

CPU 41 is a central processing unit that manages the entire operation control of the data analyzer.

ROM (Read Only Memory) 42 is a memory wherein the basic control program to be executed by CPU 41 is stored beforehand. When the data analyzer is booted up, the basic operation control of the entire data analyzer is performed by CPU 41 by enabling CPU 41 to execute the basic control program.

RAM (Random Access Memory) 43 is a memory which is used as a work memory when CPU 41 executes various control programs and is also used as a main memory, when required, as a temporary storage area for various data.

HDD 44 is a hard disk drive device that functions as the knowledge source DB 35 shown in FIG. 3 and stores the background information that can be used by the user beforehand. In addition, various control programs which enable CPU 41 to function as the data analysis unit 31, the knowledge data management unit 32, and the analysis result selection unit 33 as shown in FIG. 3 are stored beforehand in the HDD 42. These control programs are read out and executed by CPU 41 after CPU 41 executes the basic control programs.

The input unit 45 obtains input corresponding to various instructions from the user and input of the experimental data 30, and comprises various input devices such as a keyboard and a mouse, reading devices for mobile-type recording-media such as FD (Flexible Disk), CD-ROM (Compact Disc-ROM), DVD-ROM (Digital Versatile Disc-ROM), MO (Magneto-Optics) Disks, or interface device capable of transferring data with other devices.

The presentation unit 46 presents various information corresponding to instructions from CPU 41 and comprises CRT (Cathode Ray Tube) or LCD (Liquid Crystal Display), for example.

The data analyzer shown in FIG. 4 is configured comprising the foregoing components. In addition, since most standard computers have the configuration shown in FIG. 4, the present invention can also be implemented by computers such as these.

Next, described are the details of control processing executed by CPU 41 in FIG. 4. In the description below, analysis of expression quantity measured by changing experimental conditions (cell type, changes in cell conditions accompanying the lapse of time, etc.), in connection with a plurality of genes, is used as an example.

Figure 5:
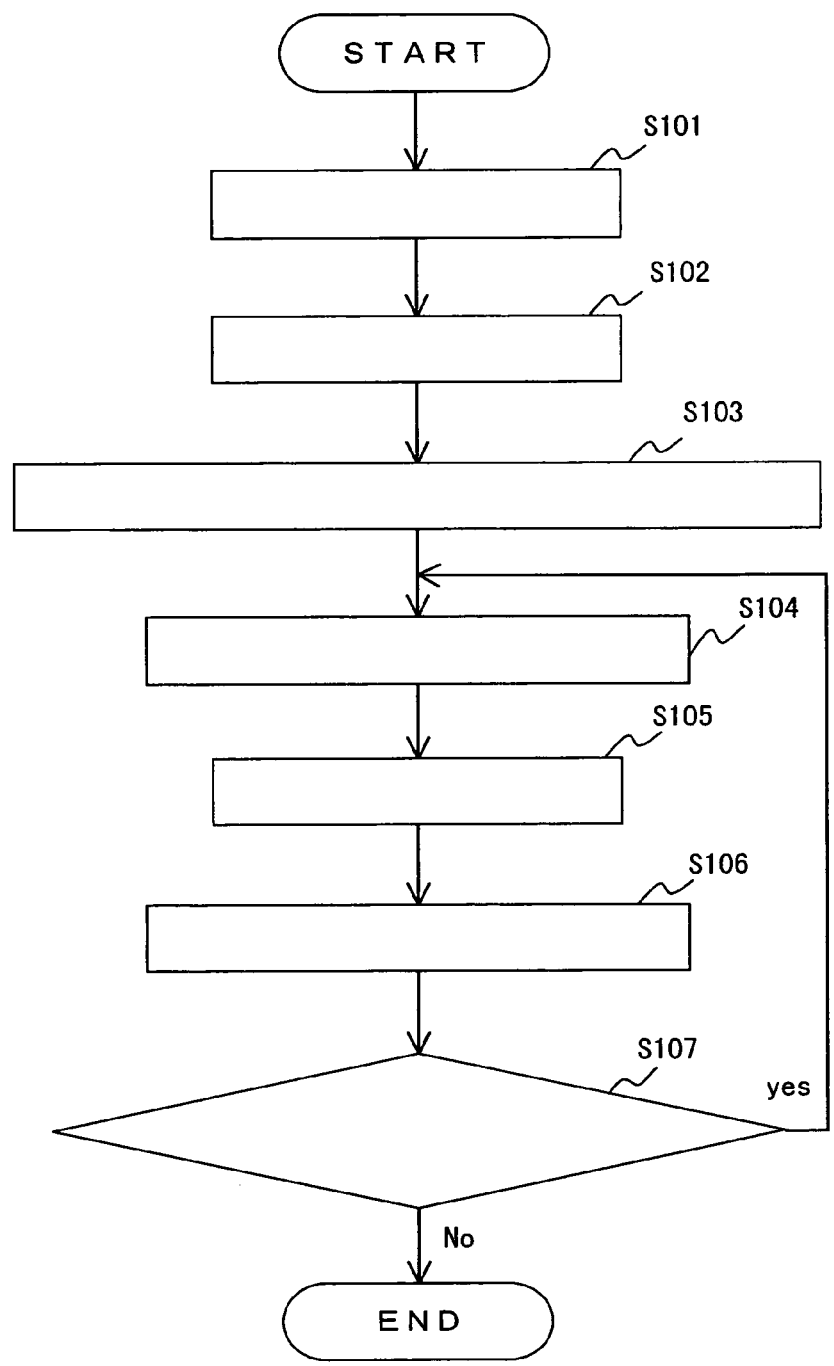
FIG. 5 is a flowchart showing the processing details of a control processing performed by a CPU.

FIG. 5 is a flowchart showing the processing details of control processing executed by CPU 41. The functions of various configurations of the data analyzer shown in FIG. 3 are realized in the configuration shown in FIG. 4 by enabling CPU 41 to execute the control processing shown in FIG. 5.

The processing shown in FIG. 5 is started after the data analyzer shown in FIG. 4 is booted, the basic control program stored in ROM 42 is read out and executed by CPU 41, and a predetermined initialization processing is executed.

In FIG. 5, an acquisition processing for experimental data 30, or in other words, a processing to acquire experimental data 30 which is to be input to the input unit 45 is first executed in S101.

An analytical processing of the experimental data 30, which is the function of the data analysis unit 31 in FIG. 3, is executed in S102. Ordinarily, since there can be a plurality of analytical viewpoints in the analysis of data, a plurality of analytical results are found for each analytical viewpoint in this data analytical processing. In the embodiment according to the present invention, analysis of the experimental data 30 is performed by factor analysis which is one system of multivariable analysis.

Here, analysis of the experimental data 30 by factor analysis is described by using FIGS. 6A, 6B, and 6C.

FIG. 6A is a table showing an example of the data to be analyzed, which is the experimental data 30. The table adds up the expression quantities in condition 1, condition 2, - - - condition n for genes of differing types, gene-1, gene-2, - - - For example, d (1, 2) indicates the expression quantity (numerical value) of gene 1 in condition 2.

FIG. 6B is a table showing the results of a factor analysis performed on the data to be analysis shown in FIG. 6A. The factor analysis is a multivariable analysis method that finds factors (as few as possible) for describing the correlation of a number of variables.

In factor analysis, the factors for describing the correlations between analytical data can be found in descending order from the most highly descriptive. Each column in the table corresponds to these factors. In addition, the value v in the table shows the factor score. The factor score is a value indicating the characteristics of various genes relative to the factors (vertical axis). For example, the factor score of the second factor of the gene, gene-1, is v (1, 2).

Although it is determined that, in the embodiment according to the present invention, data analysis is performed through factor analysis, it is possible to obtain similar results even if, for example, other multivariable analytical methods such as main component analysis are used.

FIG. 6C shows a representation example by scatter diagram which is one of the common presentation methods of factor analytical results. Although, as in this example, the factor analytical results are mostly expressed in a graphical form by selecting two highly descriptive axes (the first factor and the second factor), user interpretation is frequently supported by enabling presentation wherein the axis is replaced by another factor in accordance with instruction from the user. Furthermore, in this presentation example, the afore-mentioned factor rotation method (varimax method) can be perceived as a method for automatically selecting an easily interpretable projection surface (presentation plane) in a space using a highly descriptive factor as the axis.

Returning to the description of FIG. 5, in S103, an acquisition processing of knowledge data related to experimental data 30, or in other words, a processing which acquires knowledge data related to experimental data 30 from the knowledge source DB 35 stored in HDD 44 beforehand, is performed. This processing is performed in knowledge data management unit 32 in FIG. 3. The details of the processing are described.

As stated above, in the embodiment according to the present invention, the knowledge source DB 35 comprises protein DB 35-1, gene DB 35-2 and document DB 35-3. The knowledge data management unit 32 extracts knowledge data from these knowledge sources DB 35 in a form in which the attribute and the attribute values of each gene correspond to each other by the following procedures, and provides the data to the analysis result selection unit 33.

[1] Extraction of Knowledge Data from Protein DB 35-1

The protein entry related to the gene is retrieved, and the feature quantity stated therein is determined to be the attribute value of the relevant gene. The method for normalizing the feature quantity into an attribute name—attribute value form is the same as that for attribute extraction from the gene DB 35-2 described next.

[2] Extraction of Knowledge Data from Gene DB 35-2

The entry related to the gene is retrieved, and the feature quantity described therein is determined to be the attribute value as is or by normalization. If the feature of the gene is described in a natural language, the knowledge data of the gene comprising a combination of the attribute and the attribute value is obtained by executing the same procedure as that for data extraction from the document DB 35-3 described later.

[3] Extraction of Knowledge Data from Document DB 35-3

The document entry related to the gene is retrieved, the major keyword contained in the document is determined to be an attribute, and whether or not the keyword appears, the number of appearances, the normalized value of the number of appearances, and the like are determined to be the attribute values. If a keyword is given to each document, this keyword is determined to be the attribute, and the attribute value is found by the same procedure. In addition, if the feature quantity is stated in the document, the attribute name-attribute value combination is found by the same procedure as that in the attribute extraction from the gene DB 35-2.

If constant exhaustive acquisition of knowledge data for all genes cannot be expected, it is preferable that the attributes of a gene group to be analyzed that can be exhaustively acquired (highly exhaustive attributes) are selected and are utilized as knowledge data. Furthermore, if the number of attributes that can be acquired is high, it is preferable that the importance of the attribute is evaluated, and the attribute whose importance has been evaluated to be high is selected as the attribute that is utilized as the knowledge data. Attribute selection for these purposes are performed, for example, as below. Moreover, the attributes may be selected in accordance with the instruction from the user (if the instruction from the user is given, this selection method is executed).

[1] Selection of Highly Exhaustive Attributes

An attribute is selected as a highly exhaustive attribute only if the threshold value of the gene that has acquired the attribute, out of the genes contained in the gene group to be analyzed, is higher than the predetermined threshold value. The threshold value that is used at this time may be defined beforehand in a form of rate, or it may be a rate specified by the user.

[2] Selection of Attributes with High Importance

The degree of importance in adopting a feature quantity as the attribute is defined beforehand, in regards to the feature quantity described in the database entry. The weighting technique for keywords, widely known in the field of information retrieval, is incorporated for the keyword attribute. For example, the value found by the following formula (invert document frequency) is used as the evaluation standard for the importance of keyword attributes:

$df$=log {(total documents)/(number of documents in which keywords appear)}

Next, a detailed procedure for acquiring knowledge data is described, taking protein DB 35-1 as an example.

First, FIG. 7 is described. This figure shows one example of an entry of the protein DB 35-1. In this example, SWISS-PROTDB entry exemplified in the following document is simplified and only parts required for the description are shown.

Amos Bairoch and Rolf Apweiler, "SWISS-PROT Protein User Manual" (Release 40), 2001 (http://www.genome.ad.jp/dbget-bin/show_man?swissprot)

As shown in FIG. 7, this entry has "field name" data which is the name of the field, "type" data showing the data type of the actual data, and "value" data which is the entity of the data for each field.

Next, FIG. 8 is described. This figure is a flowchart showing the processing details for acquisition processing of the knowledge data which is the processing in S103 in FIG. 5.

First, in S201, a retrieval processing of the knowledge data, or in other words, a processing where the knowledge data regarding the gene of experimental data 30 is retrieved and extracted from the knowledge sources DB 35, is executed.

In S202, a creation processing for an attribute name-attribute value list, or in other words, a processing where the knowledge data extracted by the processing in the previous step is converted into a list comprising a combination of attribute name-attribute value, is executed.

In S203, a selection processing of the attribute, or in other words, a processing where evaluation is performed on each combination of the attribute name-attribute value obtained by the processing in the previous step based on the viewpoints of exhaustivity or importance as stated above, and the combination that is presumed to be effective in the data analysis is selected based on the evaluation result, is performed.

The acquisition processing of the knowledge data is completed when these processes have been finished.

If the acquisition processing of knowledge data shown in FIG. 8 is performed on protein DB 35-1 where the entry shown in FIG. 7 is stored, the knowledge data management unit 32 first performs a keyword search using the gene name of the experimental data 30 as the keyword for the retrieval object of the relevant gene fields in FIG. 7, and as a result, the relevant protein entry is acquired (S201). Subsequently, a list of attribute name-attribute value is created from the fields of various acquired entries (S202). Afterwards, an evaluation is performed from the viewpoints of exhaustivity or importance as stated above, and based on the evaluation, the combination that is presumed to be effective in the data analysis is selected (S203).

Figure 9:
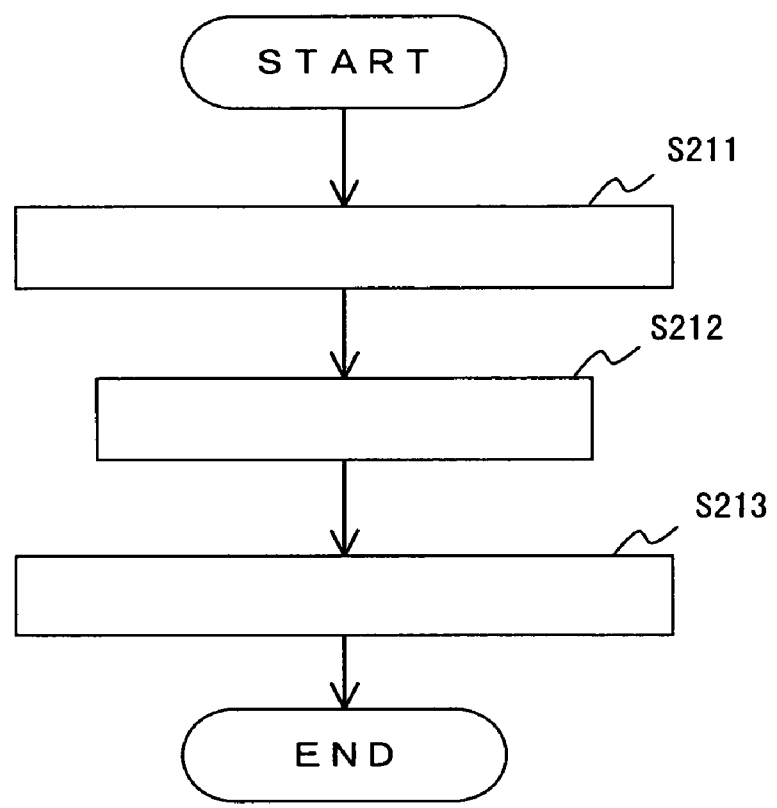
FIG. 9 is a flowchart showing the processing details of a creation processing for the attribute name-attribute value list when the data type in the field which is the object of attribute extraction is a "numerical value" type.
Figure 10:
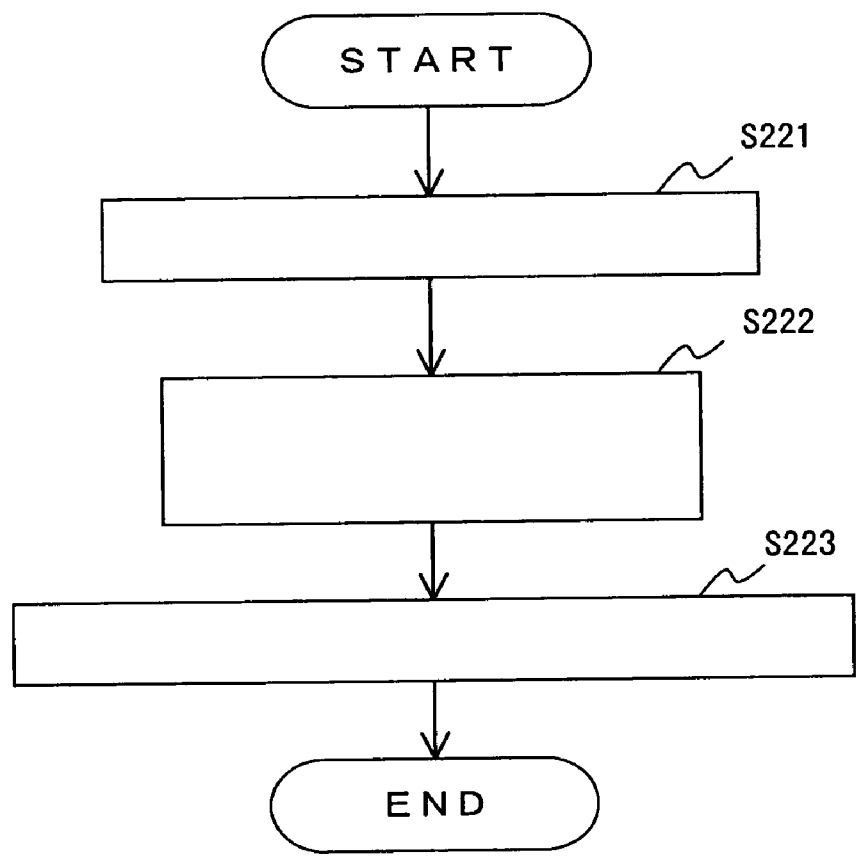
FIG. 10 is a flowchart showing the processing details of a creation processing for the attribute name-attribute value list when the data type in the field which is the object of attribute extraction is a "text" type.
Figure 11:
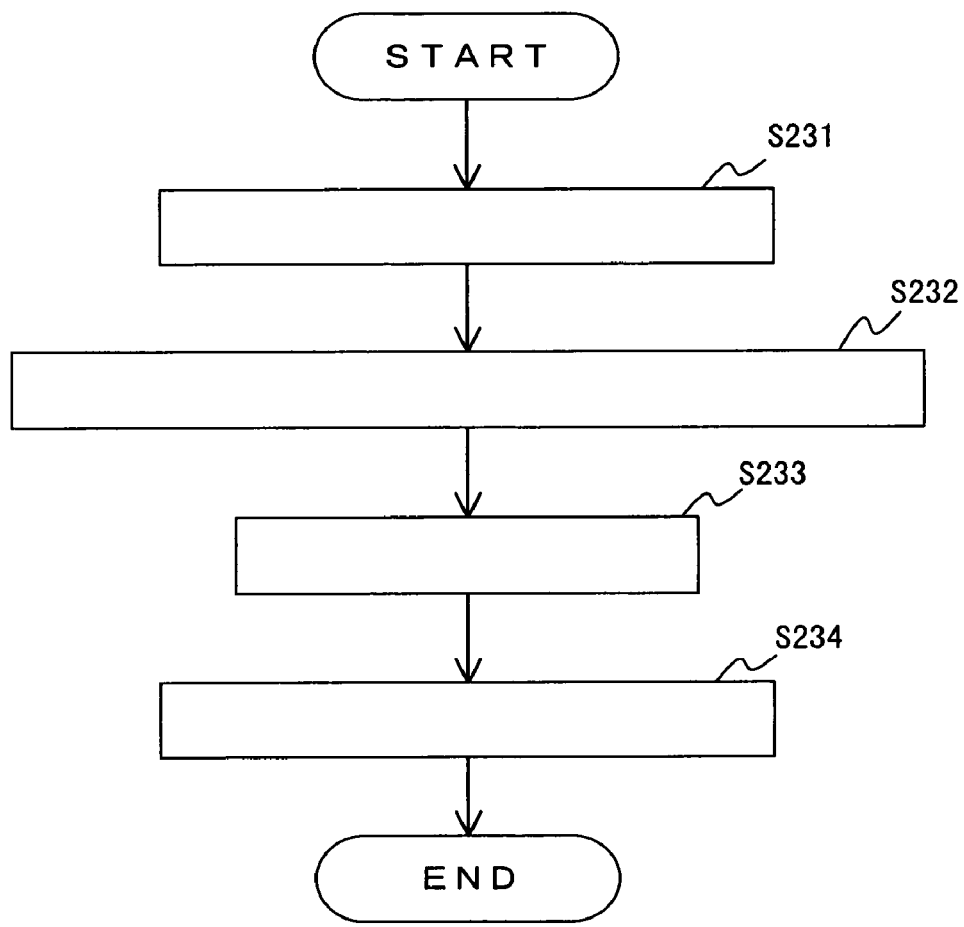
FIG. 11 is a flowchart showing the processing details of a creation processing for the attribute name-attribute value list when the data type in the field which is the object of attribute extraction is a "sequence data" type.

Next, FIG. 9, FIG. 10 and FIG. 11 are described. Each of these diagrams shows the processing details of creation processing of the attribute name-attribute value list which is the processing in S202 in FIG. 8, in the form of a flowchart.

FIG. 9 shows the processing details for when the data type of the field from which the attribute is extracted is a "numeric value" type.

In FIG. 9, first, a field extraction processing, or in other words, a processing where the objective field is extracted from the data entry, is performed in S211.

In the subsequent S212, a creation processing of the attribute name based on the field name, or in other words, a processing where the "field name" shown in the objective field extracted by the processing in the previous step is determined to be the attribute name, is performed.

In S213, a preparation processing of attribute value based on the numeric data, or in other words, a processing where the entity of the "numeric" type data shown in the objective field extracted by the processing in S211 is determined to be the attribute value, is performed.

The processes shown in FIG. 9 are completed when the foregoing processes have been completed.

If the processes shown in FIG. 9 are performed on, for example, the "molecular weight" field of the entry shown in FIG. 7 where the data type is the "numeric" type, this "molecular weight" field is first extracted (S211); subsequently, the "molecular weight" which is the field name of the extracted field is determined to be the attribute name (S212); afterwards, the value "28968" which is the entity of the data of the "molecular weight" field is determined to be the attribute value (S213); and the extraction of the combination of the attribute name-attribute value is completed.

FIG. 10 shows the processing details of the creation processing of the attribute name-attribute value list for when the data type of the field from which the attribute is extracted is a "text" (natural language) type.

In FIG. 10, the field extraction processing, or in other words, the processing where the objective field is extracted from the data entry is performed in S221.

In the subsequent S222, a creation processing of the attribute name based on the field name and the keyword transcription, or in other words, a processing where the character string which is a combination of the "field name" shown in the objective field extracted by the processing in the previous step and the transcription of the keyword in the field is determined to be the attribute name, is performed.

In S223, a preparation processing of the attribute value based on the frequency of appearance of the keyword, or in other words, a processing where the frequency of the appearance of the keyword in the entity of the "text" type data shown in the objective field extracted by the processing in S221 is determined to be the attribute value, is performed.

The processes shown in FIG. 10 are completed when the foregoing processes have been completed.

If the processes shown in FIG. 10 are performed on the "description" field of the entry shown in FIG. 7 where the data type is the "text" type for example, the "description" field is first extracted (S221) subsequently, the character string which is the combination of the "description" which is the field name of the extracted field and the transcription of the keyword in the field is determined to be the attribute value (S222); afterwards, the frequency of the appearance of the keyword in the value "(Granzyme A precursor (EC 3.4.21.78)" which is the entity of the data in the extracted field is determined to be the attribute value (S223); and the extraction of the combination of the attribute name-attribute value is completed.

FIG. 11 shows the processing details of the creation processing of the attribute name-attribute value list for when the data type of the field from which the attribute is extracted is a "sequence" type. "Sequence" data, in this case, refers to data which expresses the sequence of amino acid or bases in a symbol string. Since it is assumed, in the embodiment according to the present invention, that the attribute of the function of the gene will be utilized as the knowledge data, the field of the sequence data type is used as a guide in seeking the attribute of the function of the gene.

In FIG. 11, first, a field extraction processing, or in other words, a processing where the objective field is extracted from the data entry, is performed in S231.

In the subsequent S232, a retrieval processing of a motif DB, or in other words, a processing where the motif DB is retrieved based on the entity of the data which is the "sequence data" type shown in the objective field and the relevant motif is extracted, is performed. The motif DB is a part of the protein DB 35-1 in FIG. 3, and is a database where the partial sequences of amino acid (consensus sequence), which is commonly observed in proteins having certain functions, are stored.

In S233, a creation processing of the attribute name based on the motif, or in other words, a processing where a motif name that is given to the motif extracted by the processing in the previous step is determined to be the attribute name, is performed.

In S234, an attribute value setting processing, where the value that indicates the relation (for example, "1") is set as the attribute value, is performed. A processing where the value showing the degree of certainty of the relation between amino sequence and the motif is set as the attribute value can also be the processing detail of the attribute value setting processing.

The processes shown in FIG. 11 are completed when the foregoing processes have been completed.

If the processes shown in FIG. 11 are performed on, for example, the "amino acid sequence" field of the entry shown in FIG. 7 where the data type is the "sequence data" type, the "amino acid sequence" field is first extracted (S231); subsequently, the motif DB is retrieved based on the value "MRNSYRFLASSLSVVVSLLL - - - " which is the entity of the data of the extracted "amino acid sequence" field, and the relevant motif is extracted (S232); then, the motif name of the extracted motif is determined to be the attribute name (S233); thereafter, the value showing the relation, or the value showing the degree of certainty of the correlation between the value "MRNSYRFLASSLSVVVSLLL - - - " which is the entity of the data of the extracted "amino acid sequence" field and the motif is set as the attribute value (S234); and the extraction of the combination of the attribute name-attribute value is completed.

In regards to the creation processing of the attribute name-attribute value list for when the data type of the field from which the attribute is extracted is "sequence data", in the processing shown in FIG. 11, as a simple method for extracting the combination of the tribute name-attribute value from the motif entry, the value showing the relation, or the value showing degree of certainty of the correlation between the amino acid sequence and the motif is set as the attribute value. However, as another method, the combination of the attribute name-attribute value may be extracted so as to perform the processing shown in FIG. 10 on the functional characteristics of the motif described in the motif entry.

Returning to FIG. 5, in S104, a collation processing between the analytical results and the knowledge data, or in other words, a processing where the results of the analytical processing in S102 as stated above and the knowledge data acquired by the afore-mentioned processing in S103 are collated, is performed. Furthermore, in subsequent S105, a selection processing of the analytical results, or in other words, a processing where the analytical results that are presented to the user are selected based on the results of the collation processing in S104, is performed. The processes in S104 and S105 are those performed in the analytical result selection unit 33 in FIG. 3.

Here, FIGS. 12A, 12B, and 12C are described. These figures show a processing example of the knowledge data that is performed by the analytical result selection unit 33.

FIG. 12A is the table showing the results of the factor analysis performed on the data to be analyzed, which is the experimental data 30, and is the same table as the FIG. 6B.

The analytical result selection unit 33 acquires the knowledge data associated with the gene to be analyzed shown in each line in the table shown in FIG. 12A by performing the processing shown in FIG. 8 through the knowledge data management unit 32, re-arranges the obtained knowledge data into the form of attributes and attribute values related to each gene, and creates the table shown in FIG. 12B.

In the table showing the knowledge data in FIG. 12B, in gene-2, for example, it is expressed that the attribute value is f (2, 1) in regards to the attribute name which is attribute 1.

Next, the analytical result selection unit 13 creates a table corresponding to the synthesized matrix shown in FIG. 12C by multiplying the matrix corresponding to the table showing the analytical results (factor analytical results) shown in FIG. 12A by the matrix corresponding to the table showing the knowledge data shown in FIG. 12B. In the table in FIG. 12C, each line indicates a factor, and each column indicates an attribute. In order to calculate the matrix corresponding to this table in FIG. 12C, the transposed matrix of the matrix corresponding to the table in FIG. 12A is multiplied by the matrix corresponding to the table in FIG. 12B.

FIGS. 13A, 13B, and 13C show a calculation example for when specific numeric values are given to each column in the table shown in FIG. 12A and FIG. 12B and the synthesized matrix shown in FIG. 12C is calculated. Each table in FIGS. 13A, 13B, and 13C to which each column is given a numeric value corresponds to each table in FIGS. 12A, 12B, and 12C.

Next, analytical result selection unit 13 performs a factor analysis with the attributes as the variables on the table for the synthesized matrix in FIG. 12C which expresses the relation between the factors and the attributes. This aspect is shown in FIG. 14A and FIG. 14B.

FIG. 14A is a table for the synthesized matrix expressing the relation between the factors and the attributes, and is the same as the table in FIG. 12C. In addition, FIG. 14B is a table showing the results of a factor analysis that was performed in regards to the table in FIG. 14A with the attributes as the variables. The value w in the table is the factor score (hereinafter referred to as "synthesized factor score") which is obtained by performing factor analysis on the afore-mentioned synthesized matrix for each factor, e-1 to e-n (hereinafter referred to as "fundamental factor"), obtained by the factor analysis of the experimental data 30. In this table, the synthesized factor scores are indicated by factors c-1 to c-n (hereinafter referred to as "synthesized factor") obtained by performing factor analysis on the synthesized matrix. For example, the synthesized factor score for the synthesized factor c-2 to the fundamental factor e-1 is w (1, 2).

The processes up to the foregoing are the collation processing of S104 in FIG. 5.

Next, the analytical result selection unit 13 selects the factors used for the presentation of the analytical results based on the synthesized factor score. The selection is performed by a selection processing of the analytical results in S105. The factors selected here are adopted as the axes for the presentation of the analytical results by the graphical expression.

Although various methods can be used to select the factors, two examples of typical selection methods are shown here.

The first method is one in which the fundamental factors are selected based on the synthesized factor scores and used as the presentation axes of the graph.

In this method, first, a number of highly descriptive synthesized molecules (high contribution rate in regards to information to be analyzed) are selected from the synthesized molecules obtained as the results of a factor analysis. Next, the sum of the synthesized factor scores as the grade for the selected synthesized factors are found for each fundamental factor, and the two fundamental factors with the highest grades are selected as the presentation axes of the graph.

Figures 15A, 15B:
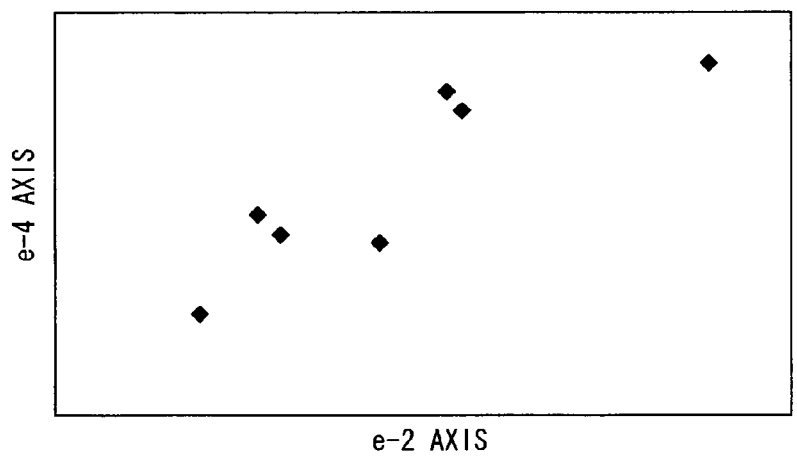
FIG. 15A is a table showing that a k-number of synthesized factors which are highly descriptive are selected out of the results of the factor analysis shown in FIG. 14B., and the sum of the synthesized factor scores as the grade for the k-number of synthesized factors are found for each fundamental factor.
FIG. 15B is an example which graphically expresses various data in a scatter diagram, using the fundamental factors e-2 and e-4 as the presentation axes if the grades of these two fundamental factors in the table in FIG. 15A are high.

The first method is described by using FIG. 15A and FIG. 15B.

FIG. 15A shows that a k-number of synthesized factors which are highly descriptive are selected out of the results of the factor analysis shown in FIG. 14B and the sum of the synthesized factor scores as the grade for the k-number of synthesized factors are found for each fundamental factor.

In the selection of the synthesized factors, although the number of selections may be preset as in FIG. 15A, a value which is called "communality" is calculated in the factor analysis obtained for each synthesized factor, and based on this value, for example, all synthesized factors with a value of communality higher than the preset value of the synthesized factors may be selected.

FIG. 15B is an example which graphically expresses various data in a scatter diagram, using the fundamental factors e-2 and e-4 as the presentation axes if the grades of these two fundamental factors in the table in FIG. 15A are high.

Here, the user of the data analyzer can easily recognize the similarities in the qualities of the genes, the correlation between the genes of similar qualities, the fundamental factors selected as the axes and the attribute (or in other words, the background knowledge of the user), and the like by graphically representing the table showing the relation between the genes and the fundamental factors shown in FIG. 6B and the table showing the relation between the fundamental factors and the attributes shown in FIG. 12C, respectively, in the scatter diagrams which use the two fundamental factors selected as stated above as the presentation axes. Furthermore, the user can easily recognize the relation between the synthesized factors, the genes, and the attributes by graphically representing the table, shown in FIG. 14B, showing the relation between the fundamental factors and the synthesized factors in the scatter diagram with the afore-mentioned two fundamental factors as the presentation axes, as well.

Described next is the second method for selecting the factors used for the presentation of the analytical results. This method presents the analytical results using the synthesized factors which are highly descriptive (high contribution rate in regards to the information for the analytical object), out of the synthesized factors obtained as the results of the factor analysis, as the presentation axes.

In this method, only the number of synthesized factors which are highly descriptive equivalent to the number of the dimensions of the graph to be expressed (for example, 2 factors if a two-dimensional graph is expressed) are selected, and subsequently, the vector with the synthesized factor scores of each fundamental factor as its component is found for each of the selected synthesized factors. Furthermore, based on the relation between the genes, the attributes and the fundamental factors and the relation between the found vectors and the fundamental factors, various genes and various attributes that are plotted in the graph with the fundamental factors as the axes are projected on the plane extended by the previously found vector. Then, a scatter diagram comprising the points projected on the plane is presented as the analytical results.

Figures 16A, 16B:
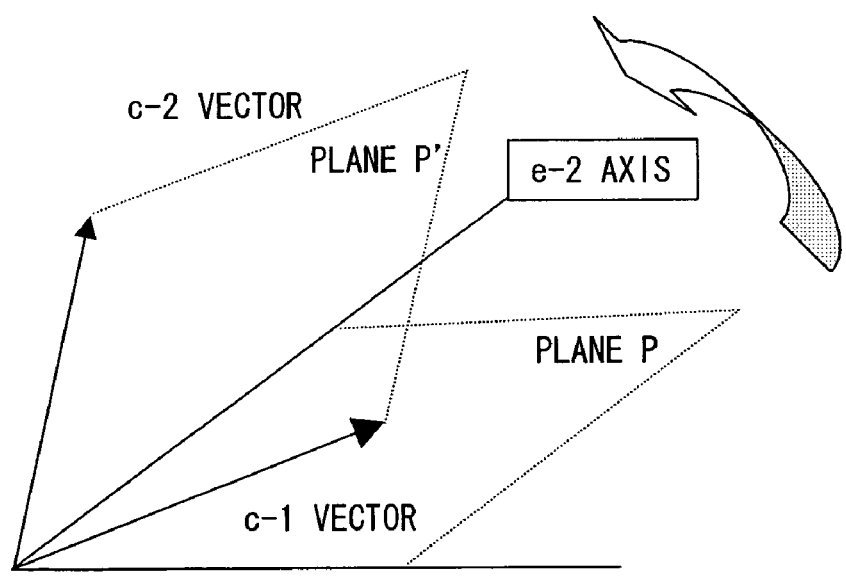
FIG. 16A is a table showing a situation wherein a total of two synthesized factors, c-1 and c-2, which are highly descriptive are selected from the results of the factor analysis shown in FIG. 14B.
FIG. 16B shows a situation wherein, for each selected synthesized factor, c-1 vector and c-2 vector of which the components are the synthesized factor scores of each fundamental factor are found, and each gene and each attribute that are plotted on the plane P with the fundamental factors as the axes are projected on the plane P' which is extended by the c-1 vector and the c-2 vector.

The second method is described by using FIG. 16A and FIG. 16B.

The table in FIG. 16A shows a situation wherein a total of two synthesized factors, c-1 and c-2, which are highly descriptive are selected from the results of the factor analysis shown in FIG. 14B.

In addition, FIG. 16B shows a situation wherein, for each selected synthesized factor, c-1 vector and c-2 vector of which the components are the synthesized factor scores of each fundamental factor are found, and each gene and each attribute that are plotted on the plane P with the fundamental factors as the axes are projected on the plane P' which is extended by the c-1 vector and the c-2 vector. Thereafter, a scatter diagram comprising the points projected on the plane P' is presented to the user as the analytical results. Therefore, the user of the data analyzer can easily recognize the similarities between the qualities of the genes, the correlation between the genes of similar qualities, the fundamental factors selected as the axes, and the attributes (or in other words, the background knowledge of the user), and the like from the scatter diagram which is made from the points projected on the plane P' and uses C-1 vector and C-2 vector as the axes.

Returning to FIG. 5, in S106, a presentation processing of the analytical results and the relevant tables, or in other words, a processing for presenting the scatter diagram shown in FIG. 15B and the scatter diagram expressed on plane P' of FIG. 16B with the table showing the relation between the genes and the fundamental factors shown in FIG. 6B, the table showing the relation between the fundamental factors and the attributes shown in FIG. 12C, or the table showing the relation between the fundamental factors and the synthesized factors shown in FIG. 14B in the presentation unit 46, is performed. This processing is that which is performed in the analytical result presentation unit 34 in FIG. 3.

Thereafter, in S107, a judgment processing on whether or not the specification of an attribute regarding a new viewpoint of the analysis performed by the user who referred to the scatter diagram and the table shown in the presentation unit 46 by the processing in the previous step has been acquired by the input unit 45. If the judgment result is Yes, the processing is retuned to S104, and the processing where the analytical results using the factors with high factor scores as the presentation axes for the attributes specified by the user is presented is performed. On the other hand, if the result of the judgment processing in S107 is No, the processing in FIG. 5 is finished. The processing in S107 is performed in the analytical result presentation unit 34 in FIG. 3.

By performing the processing in FIG. 5, described thus far, by CPU 41, a data analyzer with which the user can efficiently proceed with the analyses of the experimental and search data can be realized.

The various processes shown in FIG. 5, FIG. 8, FIG. 9, FIG. 10 and FIG. 11, described thus far, and a computer executable control program are recorded in a recording media which can be read by a computer. The present invention can be also executed by a computer by reading out the program from the recording media and executed it by the computer.

Figure 17:
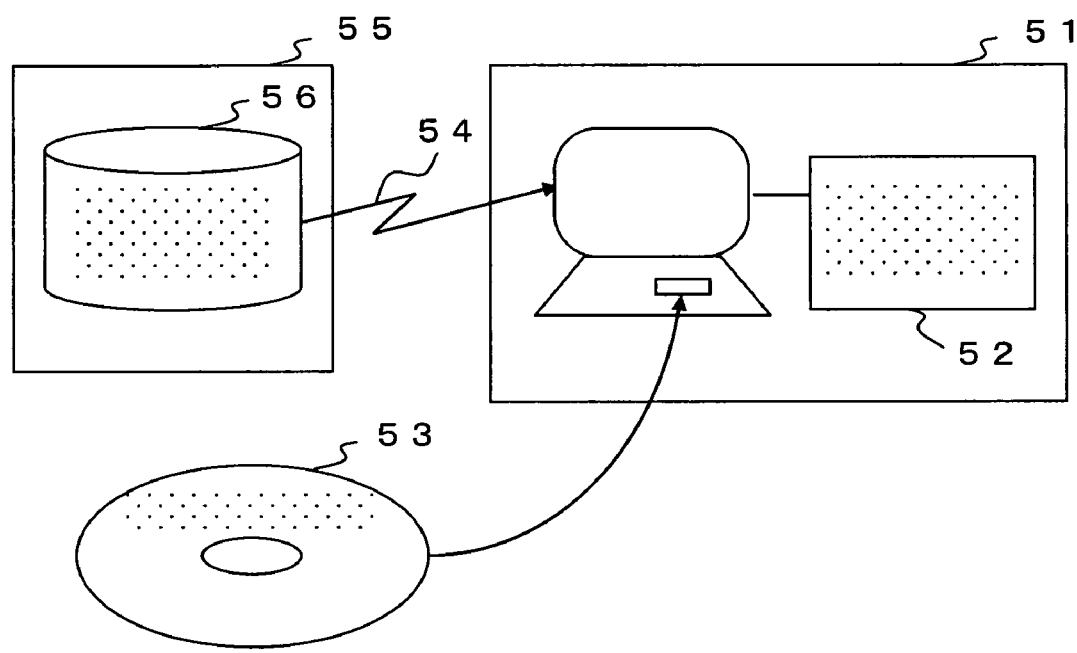
FIG. 17 is a diagram showing an example of a recording medium whose recorded program can be read by a computer.

Examples of recording media capable of having the recorded control program read out with a computer is shown in FIG. 17. As shown in this figure, memory device 52 such as RAM which embedded within the computer 51, RAM and ROM which is provided as an external peripheral device, and hard disk device, or mobile recording media 53 such as a flexible disk, MO (magneto-optical disk), CD-ROM, DVD-ROM and the like can, for example, be utilized as a recording medium. In addition, the recording medium can be memory device 56 is comprised in a computer which functions as program server 55 which is connected to the computer 51 through a communication line 54. In this case, the transmission signal obtained by modulating the carrier with the data signal expressing the control program is transmitted through the communication line 54 which is the transmission medium from the program server 55, the computer 51 demodulates the received transmission signal to regenerate the control program, and thereby, the control program can be executed.

As described in detail above, according to the present invention, since analytical results which have a high consistency with the background knowledge of the user stored in the knowledge sources DB are selected, out of a plurality of the analytical results found by performing the data analyses, and the selected results are preferentially presented to the user, analytical results that can be easily understood by the user can be presented.

The present invention is not limited to afore-mentioned embodiments, and various improvements and modifications can be made.

The present invention can be used to support the analyses of various data, and in particular, it is preferable if it is used to support the analyses of gene expression patterns for finding the correlation between the functions of the genes and between the products of the genes.

What is claimed is:

1. A data analyzer for supporting analysis of data acquired from an experiment or research performed on a set of analytical objects, comprising:
    a knowledge storage unit storing knowledge information containing text data or numeric data that describes attributes of each analytical object;
    an extraction unit acquiring the knowledge information from said knowledge storage unit and extracting, for each analytical object, attribute information including an attribute name being a name of an attribute pertaining to an analytical object and an attribute value indicating characteristics of the object in the attribute;
    a data analysis unit extracting a plurality of explanatory factors by performing a multivariable analysis with an experiment condition or research item as a variable on the result of an experiment or research given in the form of relation data between the analytical object and an experiment condition or research item, elements of the relation data being numeric data indicating characteristics of each analytical object pertaining to each experiment condition or research item; and
    an analytical result selection unit selecting an analytical result to be output by
    generating relation data between the explanatory factors and the attribute by associating through the analytical object and aggregating the explanatory factors extracted by said data analysis unit and the attribute information extracted by said extraction unit,
    obtaining a numeric value indicating a degree of consistency between each explanatory factor and the attribute information by performing a multivariable analysis with the attribute as a variable on the relation data between the explanatory factor and the attribute generated, and
    determining the explanatory factor to be used for an output of the analytical result based on the numeric value obtained.

2. A data analyzer according to claim 1, wherein said analytical result selection unit uses a keyword appearing in the text associated with said analytical object as said attribute, and performs said selection.

3. A data analyzer according to claim 1, wherein said analytical result selection unit uses said attributes which can be acquired for a predetermined number of said analytical objects or more from said knowledge information, and performs said selection.

4. A data analyzer according to claim 1, wherein said analytical result selection unit selects explanatory factors corresponding to said numeric value indicating a degree of consistency, and selects the analytical result expressed by the selected explanatory factors to be the analytical result of said selection.

5. A data analyzer according to claim 1, wherein said explanatory factors used in said analytical result selection unit are synthesized explanatory factors.

6. A data analyzer according to claim 1, wherein said analytical result selection unit outputs said explanatory factor to be used for output.

7. A data analyzer according to claim 1, wherein said analytical result selection unit further outputs the analytical result expressed by the explanatory factor specified by the user.

8. A data analyzer for supporting the analysis of data acquired as the result of an experiment or research performed on a set of analytical objects, comprising:

knowledge storage means for storing knowledge information containing text data or numeric data that describes attributes of each analytical object;

extraction means for acquiring the knowledge information from said knowledge storage means and extracting, for each analytical object, attribute information including an attribute name being a name of an attribute pertaining to an analytical object and an attribute value indicating characteristics of the object in the attribute;

data analysis means for extracting a plurality of explanatory factors by performing a multivariable analysis with an experiment condition or research item as a variable on the result of an experiment or research given in the form of relation data between the analytical object and an experiment condition or research item, elements of the relation data being numeric data indicating characteristics of each analytical object pertaining to each experiment condition or research item; and analytical result selection means for selecting an analytical result to be output by generating relation data between the explanatory factors and the attribute by associating through the analytical object and aggregating the explanatory factors extracted by said data analysis means and the attribute information extracted by said extraction means;

obtaining a numeric value indicating a degree of consistency between each explanatory factor and the attribute information by performing a multivariable analysis with the attribute as a variable on the relation data between the explanatory factor and the attribute generated in said generating; and determining the explanatory factor to be used for an output of the analytical result based on the numeric value obtained in said obtaining.

9. A data analyzing method for supporting the analysis of data acquired as the result of an experiment or research performed on a set analytical objects, comprising:

storing beforehand knowledge information containing text data or numeric data that describes attributes of each analytical object;

acquiring the knowledge information from said storing and extracting, for each analytical object, attribute information including an attribute name being a name of an attribute pertaining to an analytical object and an attribute value indicating characteristics of the object in the attribute;

extracting a plurality of explanatory factors by performing a multivariable analysis with an experiment condition or research item as a variable on the result of an experiment or research given in the form of relation data between the analytical object and an experiment condition or research item, elements of the relation data being numeric data indicating characteristics of each analytical object pertaining to each experiment condition or research item; and selecting an analytical result to be output by generating relation data between the explanatory factors and the attribute by associating through the analytical object and aggregating the explanatory factors extracted by said extracting and the attribute information extracted by said acquiring;

obtaining a numeric value indicating a degree of consistency between each explanatory factor and the attribute information by performing a multivariable analysis with the attribute as a variable on the relation data between the explanatory factor and the attribute generated in said generating; and determining the explanatory factor to be used for an output of the analytical result based on the numeric value obtained in said obtaining.

10. A computer-readable medium encoded with a computer program for enabling a computer to support the analysis of data acquired as the result of an experiment or research performed on a set of analytical objects is stored, the program when executed by the computer, causes the computer to execute the method, comprising:

storing beforehand the knowledge information containing text data or numeric data that describes attributes of each analytic object;

acquiring the knowledge information from said storing and extracting, for each analytical object, attribute information including an attribute name being a name of an attribute pertaining to an analytical object and an attribute value indicating characteristics of the object in the attribute;

extracting a plurality of explanatory factors by performing a multivariable analysis with an experiment condition or research item as a variable on the result of an experiment or research given in the form of relation data between the analytical object and an experiment condition or research item, elements of the relation data being numeric data indicating characteristics of each analytical object pertaining to each experiment condition or research item; and selecting an analytical result to be output by generating relation data between the explanatory factors and the attribute by associating through the analytical object and aggregating the explanatory factors extracted by said extracting and the attribute information extracted by said acquiring;

obtaining a numeric value indicating a degree of consistency between each explanatory factor and the attribute information by performing a multivariable analysis with the attribute as a variable on the relation data between the explanatory factor and the attribute generated in said generating; and determining the explanatory factor to be used for an output of the analytical result based on the numeric value obtained in said obtaining.

* * * * *

UNITED STATES PATENT AND TRADEMARK OFFICE
CERTIFICATE OF CORRECTION

PATENT NO. : 7,346,600 B2
APPLICATION NO. : 11/038541
DATED : March 18, 2008
INVENTOR(S) : Yoshio Nakao It is certified that error appears in the above-identified patent and that said Letters Patent is hereby corrected as shown below:

Column 16, Line 35, change "obiect" to --object--.

Column 18, Line 13, change "acguiring;" to --acquiring;--.

Signed and Sealed this

Twelfth Day of August, 2008

JON W. DUDAS
*Director of the United States Patent and Trademark Office*